(12) United States Patent
von Grünberg et al.

(10) Patent No.: US 9,307,894 B2
(45) Date of Patent: Apr. 12, 2016

(54) ENDOSCOPE COMPRISING A SYSTEM WITH MULTIPLE CAMERAS FOR USE IN MINIMAL-INVASIVE SURGERY

(71) Applicant: avateramedical GmbH, Jena (DE)

(72) Inventors: Hubertus von Grünberg, Hannover (DE); Marcel Seeber, Jena (DE); Jens-Uwe Stolzenburg, Leipzig (DE)

(73) Assignee: Avateramedical GmbH, Jena (DE)

( * ) Notice: Subject to any disclaimer, the term of this patent is extended or adjusted under 35 U.S.C. 154(b) by 188 days.

(21) Appl. No.: 13/803,226

(22) Filed: Mar. 14, 2013

(65) Prior Publication Data

US 2014/0180001 A1 Jun. 26, 2014

(30) Foreign Application Priority Data

Dec. 20, 2012 (DE) .......................... 10 2012 025 102

(51) Int. Cl.
*A61B 1/04* (2006.01)
*A61B 1/06* (2006.01)
(Continued)

(52) U.S. Cl.
CPC ................ *A61B 1/05* (2013.01); *A61B 1/00064* (2013.01); *A61B 1/00183* (2013.01);
(Continued)

(58) Field of Classification Search
CPC ........ A61B 1/012; A61B 1/0125; A61B 1/04; A61B 1/05; A61B 1/053; A61B 1/06; A61B 1/0607; A61B 1/0615; A61B 1/0623; A61B 1/0661; A61B 1/0676; A61B 1/0684; A61B 1/00179; A61B 1/00183; A61B 1/00193
USPC ........... 600/11–114, 160, 166, 174, 175–176; 606/130; 604/264
See application file for complete search history.

(56) References Cited

U.S. PATENT DOCUMENTS 5,166,787 A * 11/1992 Irion ................................ 348/75
5,305,121 A * 4/1994 Moll ................................ 348/45
(Continued)

FOREIGN PATENT DOCUMENTS

WO 2007/146987 12/2007
WO 2009/057117 5/2009
WO 2009057117 5/2009

OTHER PUBLICATIONS

International Search Report for PCT/DE2013/000805, mailed Apr. 8, 2014.

*Primary Examiner* — John P Leubecker
*Assistant Examiner* — Arnaldo Torres Diaz
(74) *Attorney, Agent, or Firm* — McDonnell Boehnen Hulbert & Berghoff LLP

(57) ABSTRACT

The present invention concerns an endoscope for minimally invasive surgery, especially for use within a surgical robotic system, which comprises a main support device (4), which basically extends over the entire length of the endoscope from the outside to the interior of the body, and which comprises at its distal end at least one illumination unit (15, 16) and two imaging devices (12a, 13a, 14a, 12b, 13b, 14b; 12c), wherein each of the imaging devices (12a, 13a, 14a, 12b, 13b, 14b; 12c) is basically arranged in such a way that it can be rotated to the outside on the same level as the main support device (4), a trocar (1), by means of which the endoscope can enter the body, and an additional support device (3), which is provided at the trocar (1) and/or the main support device (4), wherein the additional support device (3) comprises at its distal end an additional imaging device (8, 9, 10, 11), which can be rotated from the additional support device (3) to the outside and wherein the additional imaging device (7, 8, 9, 10) comprises an additional illumination unit (10, 11) and at least an additional image sensor (8, 9), which comprises a monitoring area, which encompasses the two monitoring areas of the imaging devices (12a, 13a, 14a, 12b, 13b, 14b; 12c) of the main support device (4).

6 Claims, 4 Drawing Sheets

(51) Int. Cl.
*A61B 1/05* (2006.01)
*A61B 1/00* (2006.01)
*A61B 1/313* (2006.01)
*A61B 1/32* (2006.01)
*A61B 19/00* (2006.01)
*A61B 17/34* (2006.01)

(52) U.S. Cl.
CPC .............. *A61B 1/313* (2013.01); *A61B 1/32* (2013.01); *A61B 19/5202* (2013.01); *A61B 17/3421* (2013.01); *A61B 19/2203* (2013.01); *A61B 2019/5227* (2013.01)

(56) References Cited

U.S. PATENT DOCUMENTS

| | | | | |
|---|---|---|---|---|
| 5,538,497 A * | 7/1996 | Hori | | 600/182 |
| 6,277,064 B1 * | 8/2001 | Yoon | | 600/114 |
| 6,468,265 B1 * | 10/2002 | Evans et al. | | 606/1 |
| 7,553,277 B2 * | 6/2009 | Hoefig et al. | | 600/173 |
| 7,751,870 B2 * | 7/2010 | Whitman | | 600/476 |
| 8,403,826 B1 * | 3/2013 | Zobel | | 600/109 |
| 8,562,513 B2 * | 10/2013 | Yamatani | | 600/106 |
| 8,771,169 B2 * | 7/2014 | Whitman et al. | | 600/104 |
| 8,834,358 B2 * | 9/2014 | Mckinley et al. | | 600/173 |
| 8,864,652 B2 * | 10/2014 | Diolaiti et al. | | 600/102 |
| 8,961,399 B2 * | 2/2015 | Diolaiti | | 600/114 |
| 8,992,420 B2 * | 3/2015 | Maahs et al. | | 600/114 |
| 2002/0049367 A1 * | 4/2002 | Irion et al. | | 600/173 |
| 2004/0111183 A1 * | 6/2004 | Sutherland et al. | | 700/245 |
| 2005/0234294 A1 | 10/2005 | Saadat et al. | | |
| 2005/0234296 A1 * | 10/2005 | Saadat et al. | | 600/129 |
| 2006/0252994 A1 * | 11/2006 | Ratnakar | | 600/173 |
| 2007/0032701 A1 * | 2/2007 | Fowler et al. | | 600/173 |
| 2007/0073109 A1 * | 3/2007 | Irion | | 600/179 |
| 2007/0106113 A1 * | 5/2007 | Ravo | | 600/113 |
| 2007/0255100 A1 * | 11/2007 | Barlow et al. | | 600/114 |
| 2008/0027279 A1 * | 1/2008 | Abou El Kheir | | 600/111 |
| 2008/0208006 A1 * | 8/2008 | Farr | | 600/178 |
| 2008/0275298 A1 * | 11/2008 | Ratnakar | | 600/109 |
| 2009/0062604 A1 * | 3/2009 | Minosawa et al. | | 600/104 |
| 2009/0247821 A1 * | 10/2009 | Rogers | | 600/104 |
| 2009/0259097 A1 * | 10/2009 | Thompson | | 600/109 |
| 2010/0249512 A1 * | 9/2010 | McKinley et al. | | 600/160 |
| 2011/0071347 A1 * | 3/2011 | Rogers et al. | | 600/104 |
| 2011/0230894 A1 * | 9/2011 | Simaan et al. | | 606/130 |
| 2011/0306832 A1 | 12/2011 | Bassan et al. | | |
| 2012/0035416 A1 * | 2/2012 | Fernandez et al. | | 600/102 |
| 2012/0232346 A1 * | 9/2012 | Suda et al. | | 600/114 |
| 2012/0245416 A1 * | 9/2012 | Viola | | 600/109 |
| 2015/0005643 A1 * | 1/2015 | Whitman et al. | | 600/476 |
| 2015/0105618 A1 * | 4/2015 | Levy et al. | | 600/110 |

\* cited by examiner

ENDOSCOPE COMPRISING A SYSTEM WITH MULTIPLE CAMERAS FOR USE IN MINIMAL-INVASIVE SURGERY

CROSS REFERENCE

This application claims priority to German Patent Application Serial No. DE 10 2012 025 102.5, filed Dec. 20, 2012, incorporated by reference herein in its entirety.

FIELD OF THE INVENTION

The present invention concerns an endoscope with a multi-camera system for use in minimally invasive surgeries and a respective surgical robot, especially for use in minimally invasive surgery, such as laparoscopy.

BACKGROUND

Minimally invasive surgeries, such as laparoscopic operations, are performed with the use of surgical instruments, for example, forceps, cutting and sewing tools, which are inserted into the body of a patient via one or several trocars. Usually, two to four, in most cases three surgical instruments are used. In addition to these instruments, it is required that a visualization unit is available which allows the surgeon to observe the area of operation. Such a visualization unit always comprises a camera or an endoscope, which are also inserted into the body of the patient via a trocar. Usually such visualization is performed by means of an endoscope which represents on an external monitor image of the area of operation in 2D or 3D. Prior art has provided numerous endoscopes in which a visualization unit, for example, a camera, has been integrated in the distal end. However, an endoscope can be provided with a camera either on its distal or on its proximal end. The images obtained by means of an endoscope are represented on one or several external monitors via an image transmission system and an image processing unit. Numerous endoscopes have been described in prior art.

The camera systems or endoscopes described in prior art have the disadvantage that even if two cameras are provided for taking images of the area of operation, it is not possible for these cameras to represent simultaneously in each constellation all surgical instruments due to the varying positions of the surgical instruments and the position of the endoscope near the surgical procedure, as well as the object field angle (FoV "field of view"), wherein merely the immediate area of the surgical procedure is represented. When a surgical instrument is removed from the surgical field of view, it is no longer captured by the camera or cameras and is no longer under the visual control of the surgeon or his assistant.

SUMMARY OF THE INVENTION

In one aspect, the invention provides an endoscope, which comprises
  a main support device, which basically extends over the entire length of the endoscope from the outside to the interior of the body, and which comprises at its distal end at least one lighting unit and two imaging devices, wherein each of the imaging devices is basically arranged in such a way that it can be rotated to the outside on the same level as the main support device,
  a trocar, by means of which the endoscope can enter the body, and
  an additional support device, which is provided at the trocar and/or the main support device, wherein the additional support device comprises at its distal end an additional imaging device, which can be rotated from the additional support device to the outside and wherein the additional imaging device comprises an additional lighting unit and at least an additional image sensor, which comprises a monitoring area, which encompasses the two monitoring areas of the imaging devices of the main support device.

In one embodiment, the additional image sensor comprises a wide-angle lens which is located near the distal end of the trocar when pivoted. In another embodiment, each of the two imaging devices can be rotated about a rotation axis at the distal end of the main support device, wherein the rotation axes are aligned in a plane parallel to one another. In a further embodiment, the additional support device is located between the trocar and the main support device, especially resting directly at the main support device, wherein in particular the main support device and the additional support device have a cylindrical design. In another embodiment, each of the imaging devices is arranged in such a way that it can be tilted by means of joints about the rotation axis, as well as about a further pivot axis, in orthogonal direction toward the longitudinal extension of the support device, wherein the rotary movements about the rotation axes and the rotation axes are decoupled independently of one another.

In another aspect, the invention provides a surgical robot system having at least one robotic arm on which at least one surgical instrument and/or one endoscope can be arranged, which comprises
  a main support device that basically extends over the entire length of the endoscope from the outside to the interior of the body, and which comprises at its distal end at least one lighting unit and two imaging devices, wherein each of the imaging devices is basically arranged in such a way that it can be rotated to the outside on the same level as the main support device,
  a trocar, by means of which the endoscope can enter the body, and
  an additional support device, which is provided at the trocar and/or the main support device, wherein the additional support device comprises at its distal end an additional imaging device, which can be rotated from the additional support device to the outside and wherein the additional imaging device comprises an additional lighting unit and at least an additional image sensor, which comprises a monitoring area, which encompasses the two monitoring areas of the imaging devices of the main support device, wherein provision has been made for an image processing unit, which is connected with the two imaging devices and the additional imaging device, and a visualization unit, which represents 2D image data and/or 3D image data of the imaging devices and/or the additional imaging device.

In one embodiment, the additional image sensor comprises a wide-angle lens which is located near the distal end of the trocar when pivoted. In another embodiment, the two imaging devices are arranged at the distal end of the main support device, respectively, in such a manner that they can be rotated about a rotation axis, wherein the rotation axes are aligned in a plane parallel to one another. In a further embodiment, the additional support device is located between the trocar and the main support device, especially resting directly at the main support device, wherein in particular the main support device and the additional support device have a cylindrical design. In another embodiment, each of the imaging devices is arranged in such a way that it can be tilted by means of joints about the rotation axis, as well as about a further rotation axis, in orthogonal direction toward the longitudinal extension of the support device, wherein the rotary movements about the rotation axes and the rotation axes are decoupled independently of one another.

DESCRIPTION OF THE FIGURES

The present invention is explained in more detail by means of the enclosed exemplary figures. It is shown.

DETAILED DESCRIPTION OF THE INVENTION

Figure 1:
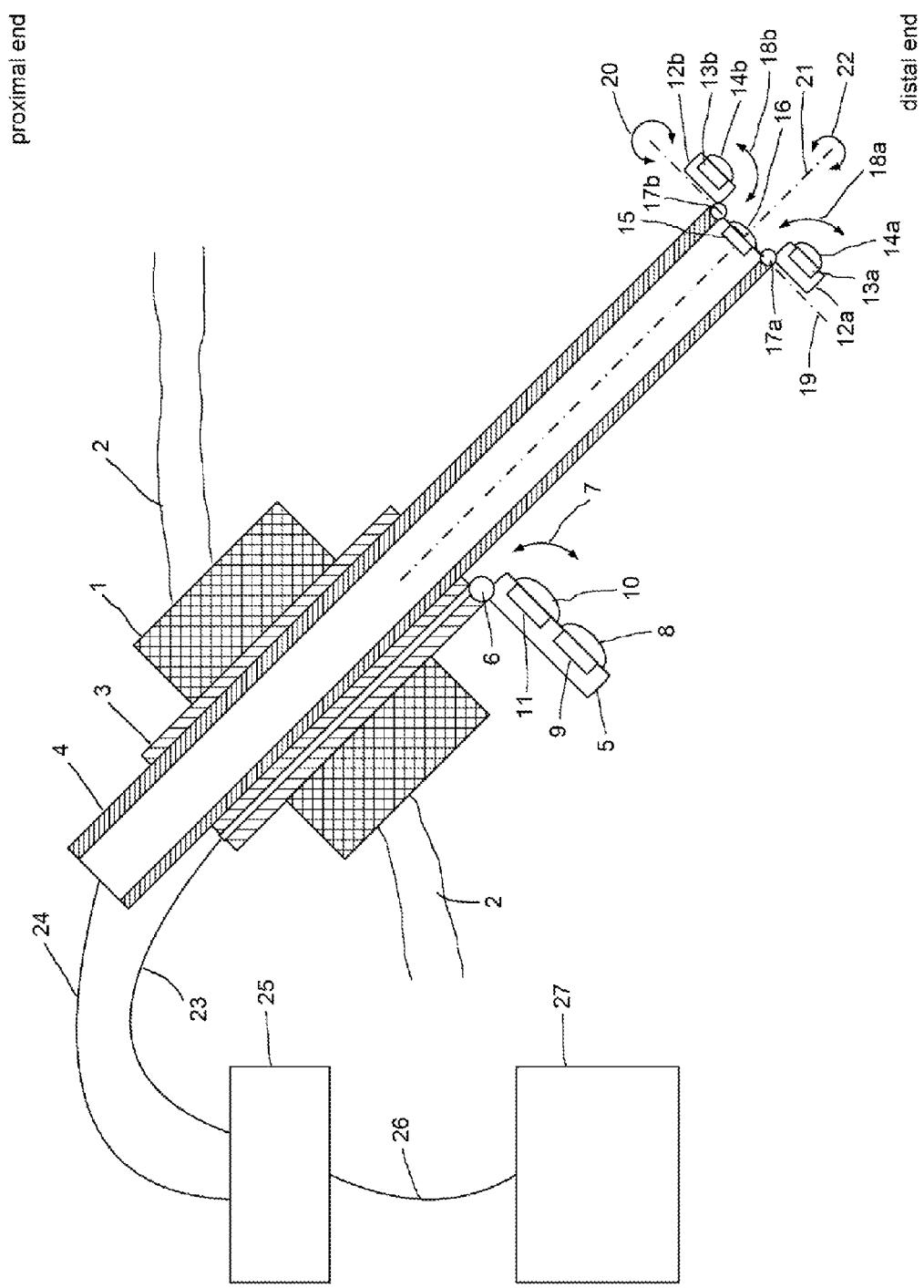
FIG. 1 is a schematic view of a designated endoscope in a preferred embodiment of a 3D detail camera which is arranged at an invention-based endoscope which is connected with an image processing unit and a visualization unit of a surgical robot system.

The invention is therefore based on the objective of providing an improved visualization system for minimally invasive surgeries, such as laparoscopic surgeries, which allows the surgeon to coordinate the instruments in a simple manner using a single trocar to access the body without having to use an additional trocar to access the body. According to the present invention, this objective is achieved by means of the endoscopes and surgical robot systems disclosed herein.

The present invention provides an endoscope with a multi-camera system for use in minimally invasive surgery, such as laparoscopy.

A first object of the present invention concerns an endoscope for minimally invasive surgery, especially for use within a surgical robot system, which basically extends over the entire length of the endoscope from the outside to the interior of the body, and which comprises at its distal end at least one lighting unit and two imaging devices, wherein each of the imaging devices is basically arranged in such a way that it can be rotated to the outside on the same level as the main support device, a trocar by means of which the endoscope can enter the body, and an additional support device, which is provided at the trocar and/or the main support device, wherein the additional support device comprises at its distal end an additional imaging device, which can be rotated from the additional support device to the outside and wherein the additional imaging device comprises an additional lighting unit and at least an additional image sensor, which comprises a monitoring area, which encompasses the two monitoring areas of the imaging devices of the main support device.

The present invention has the advantage that by means of providing and simultaneously using 2 imaging systems, an at least 2D overview camera and a 3D detail camera, which are inserted into the body of a patient via a single trocar (also combination trocar), it is possible to generate an at least 2D overview image with a high object field angle (wide angle of typically >90°) and a 3D detail image with a general object field angle of up to 70°. As a result, it is possible to represent the immediate area of operation and its surrounding area during an entire minimally invasive surgery, such as laparoscopic surgery. In this way, it is possible to represent all surgical instruments simultaneously even if due to their varying positions and the position of the camera or the endoscope, as well as the object field angle (FoV "field of view"), they are outside of the surgical field of view of both imaging devices at the distal end of the endoscope, because the additional imaging device can also capture instruments which are outside of the surgical field of view of both imaging devices. For example, this can be the case when a surgical instrument is temporarily not needed and "deposited". In most cases, such "depositing" takes place outside of the immediate surgical procedure and outside of the surgical field of view so that the instruments are not in the way during surgery. According to the invention, such "deposited" surgical elements are captured by the invention-based 2D overview camera and are therefore constantly under visual control of the surgeon or his assistant. Since the additional imaging device designed as a 2D overview camera and the imaging device designed as 3D detail camera are arranged respectively on an endoscope, for example, in the form of 2 image sensors, the surgeon has no problem to watch the picture recordings of the 2D overview camera and the 3D detail camera via a mutual or separate monitor. For the surgeon it is easy to coordinate the images because the monitoring area of the 2D overview camera, which possibly can comprise a 3D lens, encompasses the monitoring area of the 2D detail camera or is larger than the object field angle of the 3D detail camera. In this regard, it should be mentioned that an arrangement of 2 separate cameras, which are positioned completely independent and have an overlapping monitoring area not attached to the endoscope, would result in unfavorable coordination for the surgeon, possibly causing him to become "seasick" because of the two completely independent cameras. This problem is solved in a simple manner by means of the invention-based endoscope with the 2D overview camera and the adjusted 3D detail camera.

Furthermore, the lighting unit at the main support device together with the additional lighting unit at the additional support device improves the illumination of the 3D images, improving the quality of the representation of the images of the 3D detail camera.

According to a preferred embodiment of the invention, the additional image sensor comprises a wide-angle lens which is located near the distal end of the trocar when pivoted.

In particular, it is advantageous when each of the two imaging devices can be rotated about a rotation axis at the distal end of the main support device, wherein the rotation axes are aligned in a plane parallel to one another, thus minimizing the constructional expenses.

A further structural simplification involves that the additional support device is located between the trocar and the main support device, especially resting directly at the main support device, wherein in particular the main support device and the additional support device have a cylindrical design.

Furthermore, it is advantageous when each of the imaging devices is arranged in such a way that it can be tilted by means of joints about the rotation axis, as well as about a further rotation axis, in orthogonal direction toward the longitudinal extension of the support device, wherein the rotary movements about the rotation axes and the pivot axes are decoupled independently of one another.

Consequently, according to the present invention, it is possible when using only one trocar that the 3D detail camera can be moved in 4 degrees of freedom independent of the 2D overview camera. The 2D overview camera and the 3D detail camera, in turn, are connected with one another in 2 degrees of freedom, which represent the movements in x and y direction (pivot movement of the trocar) about the insertion point of the trocar into the body.

A second subject matter of the present invention concerns a surgical robot system having at least one robotic arm on which at least one surgical instrument and/or one endoscope for minimally invasive surgery can be arranged, which comprises a main support device that basically extends over the entire length of the endoscope from the outside to the interior of the body, and which comprises at its distal end at least one lighting unit and two imaging devices, wherein each of the imaging devices is basically arranged in such a way that it can be rotated to the outside on the same level as the main support device,
- a trocar, by means of which the endoscope can enter the body, and
- an additional support device, which is provided at the trocar and/or the main support device, wherein the additional support device comprises at its distal end an additional imaging device, which can be rotated from the additional support device to the outside and wherein the additional imaging device comprises an additional lighting unit and at least an additional image sensor, which comprises a monitoring area, which encompasses the two monitoring areas of the imaging devices of the main support device,
wherein provision has been made for an image processing unit, which is connected with the two imaging devices and the additional imaging device, and a visualization unit, which represents 2D image data and/or 3D image data of the imaging devices and/or the additional imaging device.

In particular, the invention-based surgical robot system has the advantage that depending on the needs the image data for the surgeon can be represented as 2D image data and/or 3D image data, i.e., the image data of the overview camera can be coupled with the image data of the 3D detail data by means of the image processing unit, providing the surgeon with a considerably improved overview through a single frame sequence on the visualization unit.

In particular, it is advantageous that the additional image sensor comprises a wide-angle lens which is located near the distal end of the trocar when pivoted.

The sub-claims show further advantageous embodiments of the invention. Accordingly, the entire disclosure of the present invention refers to the two camera systems, as well as the endoscope encompassing the two camera systems.

In minimally invasive surgery, such as laparoscopic surgery, the body of a patient is accessed via a trocar (usually through the abdominal wall or into the thorax). A surgical instrument or a camera or endoscope can be inserted into the body through such a trocar. As mentioned before, according to the invention, via a trocar two cameras are simultaneously inserted. A surgical procedure usually involves 2 to 4 surgical instruments and at least one camera. Therefore, 3 to 5 trocars are required for such a surgical procedure.

Subsequently, the present invention is described with reference to the figures:

FIG. 1 shows the invention-based multi camera system being integrated in an endoscope. The body of a patient is accessed by inserting a trocar 1 into the body tissue 2. Via a trocar 1 an additional support device 3 for a 2D overview camera is inserted into the body. The additional support device 3 is designed in such a way that a further rotationally symmetric rod-shaped main support device 4 for a 3D detail camera can be inserted into the tubular device. Alternatively, the tubular device can be used also for surgical instruments. A camera bracket 5 is attached by means of a joint 6 at the additional support device 3 in such a way that the camera bracket can be folded out through a pivot movement 7 basically by 90° to the rotation axis after being inserted into the trocar 1. The camera bracket 5 comprises an additional image sensor consisting of image sensor 9 and wide-angle lens-imaging optics 8. To illuminate the object field, the camera bracket 5 is also equipped with an additional lighting unit, consisting of a light source 11 and respective wide-angle imaging optics 10. These wide-angle imaging optics 10 are designed in such a way that the complete object field captured by the image sensor 9 and the connected wide-angle imaging optics 8 is illuminated. The camera bracket 5 with the additional image sensor and the additional lighting unit form the 2D overview camera for generating a 2D overview image. Preferably, the image sensor 9 is designed as CCD or CMOS sensor with a resolution of 1920×1080 pixels or higher.

The recorded image data are supplied via the data link 23 to a processing unit 25, which processes the image data for representation, and via a further data link 26 they are supplied to a visualization unit 27. The visualization unit 27 can represent 2D and 3D image data separately but also combined in a single image or a single frame sequence. A control unit 32 determines which image data is to be represented in what way, depending on the preferences of the surgeon.

At the end of the rotationally symmetric main support device 4 are two camera modules or two imaging devices 12a, 13a, 14a, 12b, 13b, 14b consisting in particular of 2 imaging optics 14a and 14b, respectively, mounted on two camera brackets 12a and 12b. Via the joints 17a and 17b which form the pivot axes, the camera brackets 12a and 12b are connected with the main support device 4 in such a way that they can be folded out by 90° to the rotation axis of the main support device 4 after being inserted into the body in swivel direction 18a or 18b. To illuminate the object field, a lighting unit consisting of light source 15 and imaging optics 16 is mounted at the end of the main support device 4 on which also the foldable camera brackets are attached. Furthermore, the camera brackets 12a and 12b comprise image receptors consisting of image sensors 13a and 13b and imaging optics 14a and 14b. Together these two imaging devices 12a, 13a, 14a, 12b, 13b, 14b form the 3D detail camera.

Preferably, the lighting unit consisting of light source 15 and imaging optics 16 can be designed as LED light source in the way that the radiation angle of the LED combined with appropriate imaging optics 16 is selected in such a way that the object field represented by both image sensors 13a and 13b and the associated imaging optics 14a and 14b is completely illuminated. In a modified embodiment the lighting unit at the proximal end can also comprise only imaging optics 16. In this case, the light source 30 is arranged outside the main support device 4 and therefore outside of the patient. The control commands to the light source 30 are transmitted from the processing unit 25 via the data link 31. Then the light is fed via a light conductor to an appropriate branch circuit mechanism 28. Preferably, said branch circuit mechanism 28 is designed, for example, as optical fiber bundle and conducts the light to the imaging optics 16. In a further embodiment, the branch circuit mechanism 28 can be implemented also by means of appropriate rod optics.

In a further embodiment (FIG. 3), a camera bracket 12c is located at the end of the rotationally symmetric main support device 4. Said camera bracket comprises both imaging devices 13a, 14a, 13b, 14b, which in particular consist of 2 imaging optics 14a and 14b, respectively, and mounted on a camera bracket 12c. In this arrangement, the light source 15 connected with the imaging optics 16 is also mounted on the camera bracket 12c in the center between the two imaging devices 13a, 14a, 13b, 14b. Via a joint 17c, which forms the swivel axis, the camera bracket 12c is connected with the main support device 4 in such a way that the camera bracket 12c can be folded out in a pivot movement 18c by 90° to the rotation axis of the main support device 4 after being inserted in the body.

In addition, the joint 17c is designed in such a way that the camera bracket 12c can be pivoted in the direction 20 by at least +/−90° about the pivot axis 19 located orthogonally to the rotation axis 21 of the main support device 4.

The recorded image data are supplied via the data link 24 to a processing unit 25, which processes the image data of the 3D detail camera for stereo representation, and via the data link 26 they are supplied to a visualization unit 27. The visualization unit 27 can represent 2D and 3D image data. A processing unit 25 controls which image data is to be represented in what way.

Figure 2:
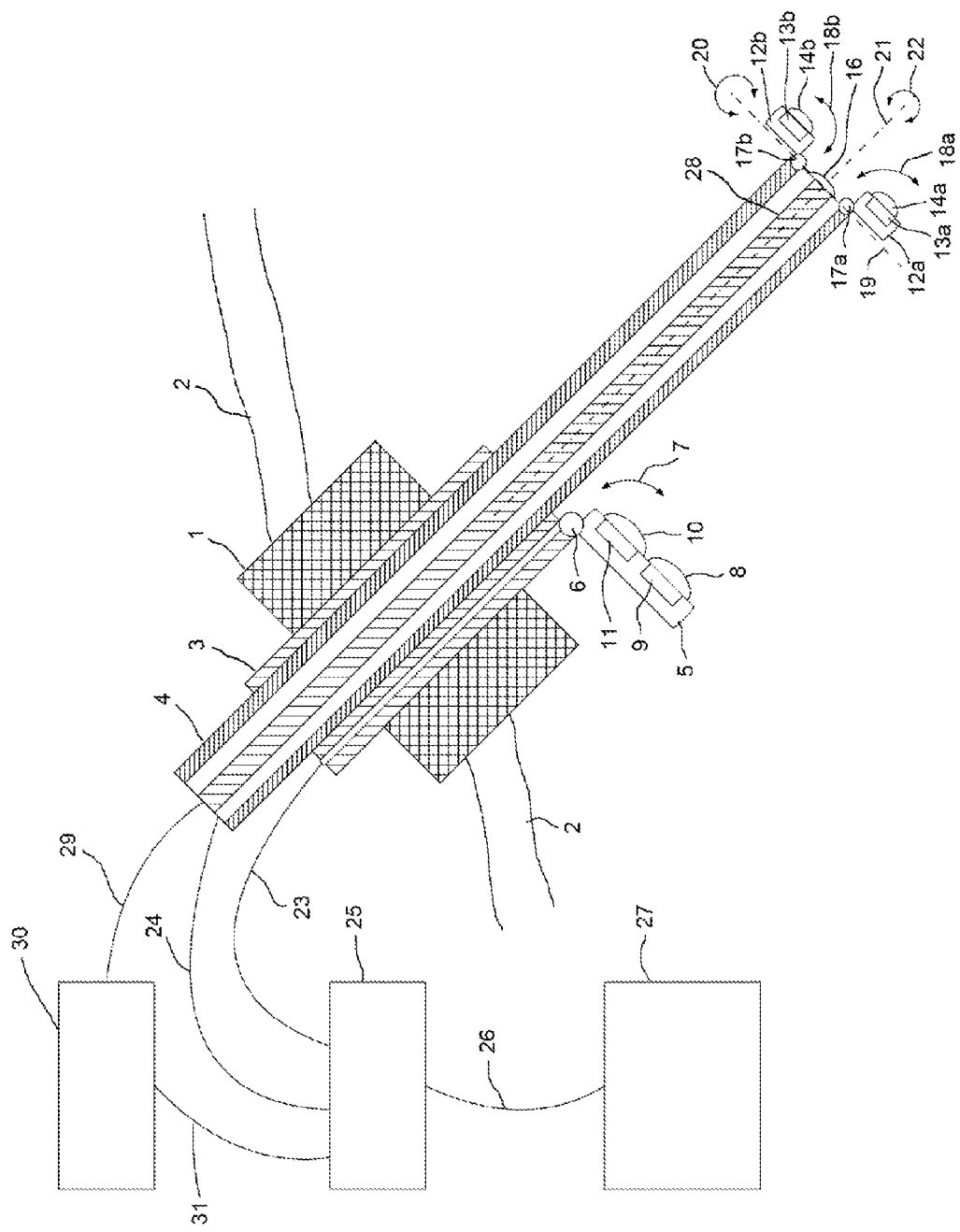
FIG. 2 is a schematic partial view of a further embodiment of a 3D detail camera with an externally connected light source which is arranged at an invention-based endoscope.

FIG. 2 shows the folding out movements of the 3D detail camera with regard to the rotation and pivot axis. The joints 17a and 17b (see FIG. 1) allow the camera brackets 12a and 12b to be folded out (see FIG. 1) by 90°, starting from the rotation axis 21 of the main support device 4.

Furthermore, the joints 17a and 17b can allow for a synchronized pivot movement or tilting by approximately +/−90° of the camera brackets 12a and 12b about the pivot axis 19 orthogonally to the rotation axis of the main support device 4. In this way, without changing the position of the main support device 4, it is possible to record respective 3D images angular to the rotation axis 21 of the main support device 4.

This invention-based synchronous pivot movement of the camera brackets 12a and 12b about the pivot axis 19 orthogonally to the rotation axis of the main support device 4 has advantages in comparison to structures of endoscopes known from prior art in which the rotation axis and the optical axis are identical, i.e., a view "with an upward inclination" or "downward inclination" requires the endoscope to be tilted by the respective angle which, in turn, requires sufficient space for movement. This can put a strain on the patient's tissue and even injure the patient. Because of the possibility of pivoting the camera bracket about the pivot axis 19, the invention-based endoscope does not have to be tilted in the customary manner. Alternatively, endoscopes known from prior art use different lenses with rigid angles, which differ from 0° and typically comprise 30°. To change the lenses, the surgeon has to interrupt the surgery, remove the endoscope lens, connect a different lens with the endoscope and again insert the endoscope into the patient by way of the endoscope trocar.

Furthermore, the joints 17a and 17b allow for an independent, decoupled pivot movement by basically +/−90°, respectively, of the camera brackets 12a and 12b about the pivot axis 19 orthogonally to the rotation axis 21 of the main support device 4. In this way, without changing the position of the main support device 4, it is possible to record respective 2D images over a larger object field angle. For this purpose, after being transmitted via the data link 24 (see FIG. 1) to a processing unit 25 (see FIG. 1) the two 2D images are composed in such a way that it is possible to represent on the visualization unit 27 (see FIG. 1) a 2D image over a larger object field angle, which is not possible when using customary endoscopes. If the visualization unit 27 is also suitable for representing 3D images, the processing unit 25 can also calculate a 3D image, which is then represented to the surgeon on the visualization unit 27 as a three-dimensional image. The surgeon is able to comprehend such a three-dimensional image on the visualization unit 27 by means of an optical aid, for example, shutter glasses or polarization glasses. Alternatively, the visualization unit 27 by means of an optical imaging system is designed in such a way that it projects a left image for the left eye and a right image for the right eye, respectively. In this embodiment, it is not required to use additional optical aids, for example, shutter glasses or polarization glasses.

Figure 3:
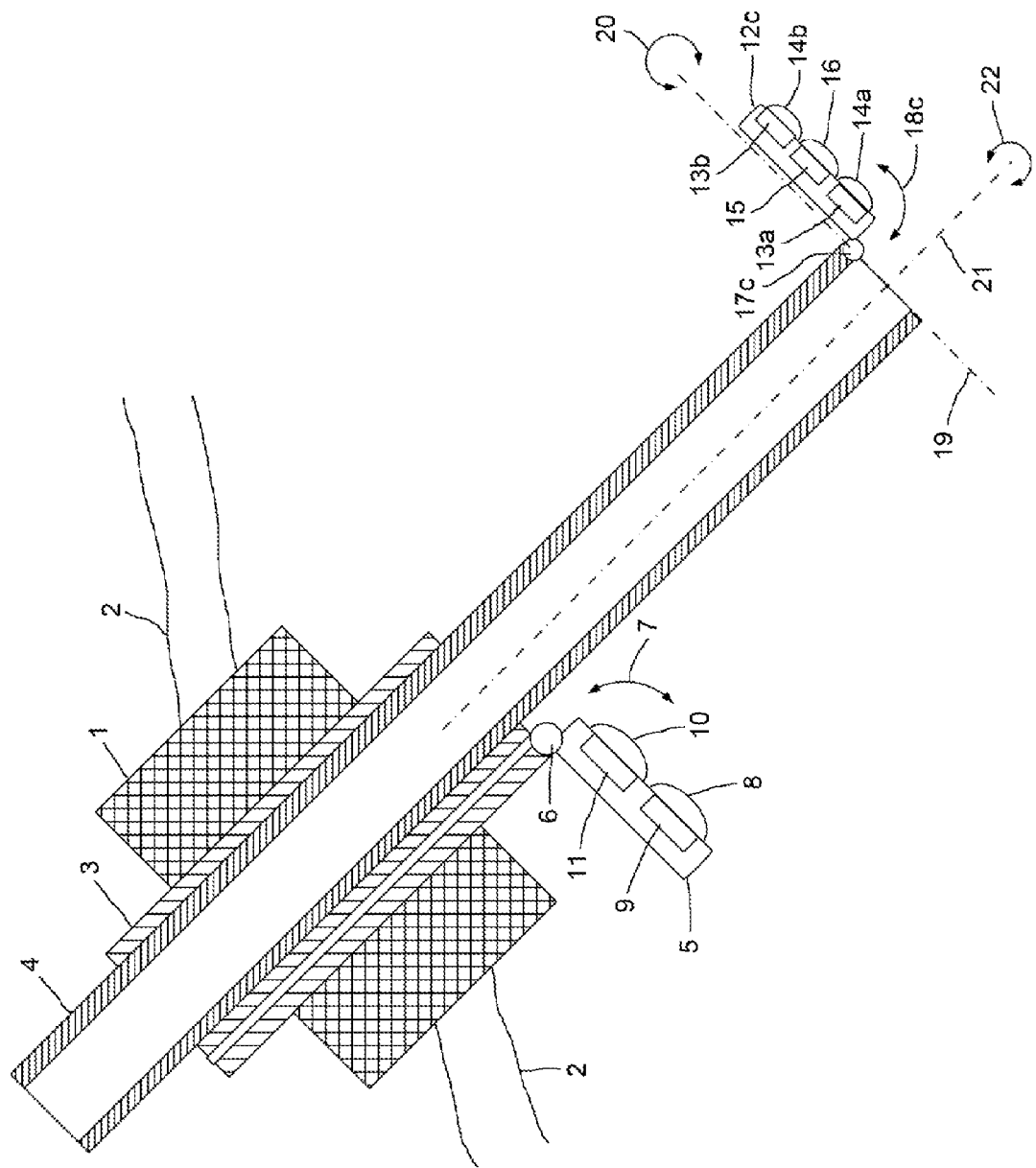
FIG. 3 is a schematic partial view of a further, preferred embodiment of a 3D detail camera which can be implemented by means of a reduced number of the mechanical control members arranged at an invention-based endoscope.

In the alternative embodiment according to FIG. 3, the camera bracket 12c comprises both imaging devices 13a, 14a, 13b, 14b, as well as the lighting unit consisting of light source 15 and imaging optics 16. Consequently, pivoting the joint 17c of the camera bracket basically by +/−90° about the pivot axis 19 located orthogonally to the rotation axis 21 of the main support device 4 has an effect on both imaging devices 13a, 14a, 13b, 14b, as well as the lighting unit consisting of light source 15 and imaging optics 16. In this embodiment it is advantageous that the imaging optics 16 can be optimally adapted to the object field angle recorded by the imaging devices 13a, 14a, 13b, 14b, because in this embodiment the lighting unit is pivoting together with the imaging devices. In this embodiment, the light source 15 is preferably designed as LED illumination.

In the processing unit 25, the position and trajectories of the inserted instruments can be calculated from the data of the 2D overview camera. This information of the trajectories can be shown as additional information when representing in an appropriate manner, for example, as overlay representation, the 3D image on the visualization unit 27.

Figure 4:
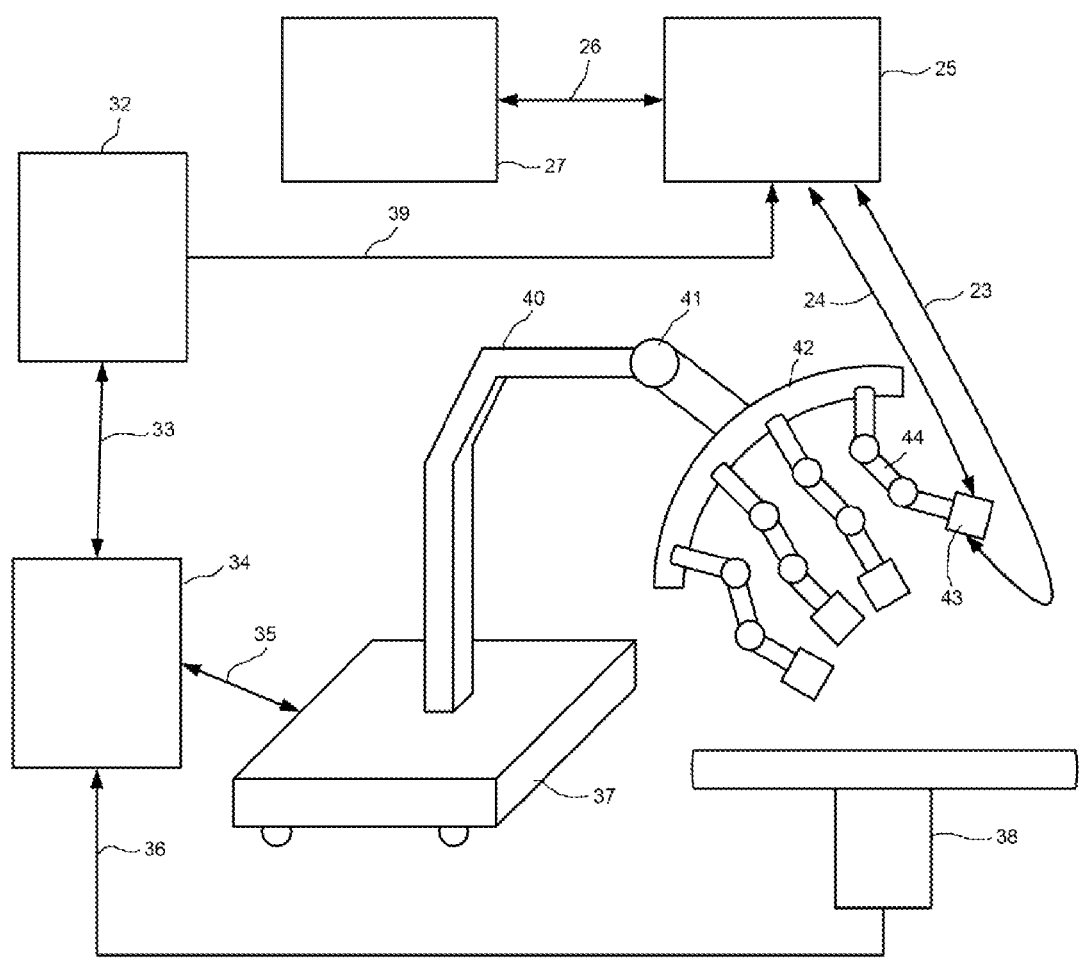
FIG. 4 is a diagram of a general view of how a visualization solution is used in a surgical robot system for use in minimally invasive surgery, for example, laparoscopy.

FIG. 4 shows the exemplary use of the invention-based multi-camera system 43 in a telemanipulator or robot system. The surgeon controls the actuators via a display or control unit 32. The control commands generated by means of the display and control unit 32 are transmitted to a control unit 34 via data transmission 33. Said control unit 34 is connected with the robot system 37 via a further data line 35 and, equipped with a support shaft 40, bowing 42 can be pre-positioned via joint mechanics according to the position of the patient on the OR table 38 in such a way that the robotic arm 44 allows for an optimal position of the multi-camera system 43. The image data recorded by the 2D overview camera are supplied via the data link 23 to a processing unit 25, which processes the image data, and via a further data link 26 they are supplied to a visualization unit 27. The visualization unit 27 can represent 2D and 3D image data, for example separately, but also combined in a single image or a single frame sequence. A control unit 32 determines which image data is to be represented in what way, depending on the preferences of the surgeon. The control commands generated by the control unit 32 are transmitted by means of the data link 39 to the processing unit 25.

According to FIG. 1, two images from different positions of a scene are recorded by two imaging devices 12a, 13a, 14a, 12b, 13b, 14b, which in particular consist of 2 imaging optics 14a and 14b, respectively, and which are mounted on 2 camera brackets 12a and 12b. The recorded image data are supplied via the data link 24 to a processing unit 25, which processes the image data of the 3D detail camera for stereo representation, and via the data link 26 they are supplied to a visualization unit 27. The visualization unit 27 can represent 2D and 3D image data. A control unit 32 determines which image data is to be represented in what way, depending on the preferences of the surgeon. The control commands generated by the control unit 32 are transmitted by means of the data link 39 to the processing unit 25.

Minimally invasive surgery, such as laparoscopic surgery, is often performed by means of surgical manipulators, telemanipulators or robot systems. The invention-based endoscopes and cameras can be used in such telemanipulators or robot systems for minimally invasive surgery, especially for use within a surgical robot system The present invention is not limited to the fact that an invention-based endoscope or invention-based camera is used in a telemanipulator or robot system in order to perform minimally invasive surgery. It can also be used in the medical field apart from such systems.

We claim:

1. An endoscope, comprising a main support device, which basically extends over an entire length of the endoscope, wherein a distal end of the main support device comprises at least one lighting unit and two imaging devices to detect two monitoring areas, wherein each of the two imaging devices is basically arranged in such a way that it can be rotated to the outside of the main support device,
a trocar, by means of which the endoscope can enter a human body,
and an additional support device, which is provided at the trocar or the main support device, wherein a distal end of the additional support device comprises an additional imaging device, wherein the additional imaging device is spaced apart in a longitudinal direction of the endoscope from the two imaging devices, and wherein the additional imaging device can be rotated to the outside of the additional support device, and wherein the additional imaging device comprises an additional lighting unit and at least an additional image sensor, wherein the additional image sensor comprises a further monitoring area, wherein the further monitoring area encompasses the two monitoring areas of the two imaging devices of the main support device, wherein the additional support device is located between the trocar and the main support device, resting directly at the main support device, wherein the main support device and the additional support device have a cylindrical design and wherein each of the two imaging devices is arranged in such a way that it can be tilted by means of separate joints about separate rotation axis, as well as about a further pivot axis, in an orthogonal direction relative to a longitudinal extension of the main support device, wherein the rotation axis and the further pivot axis are also orthogonal to one another and wherein rotary movements about the separate rotation axes are decoupled independently of one another, and the separate rotation axes are also decoupled independently of one another.

2. The endoscope according to claim 1, characterized in that the additional image sensor comprises a wide-angle lens located near a distal end of the trocar when the additional image sensor is pivoted.

3. The endoscope according to claim 1, characterized in that each of the two imaging devices can be rotated about a rotation axis at the distal end of the main support device, wherein the rotation axes are aligned in a plane parallel to one another.

4. A surgical robot system having at least one robotic arm on which at least one endoscope can be arranged, which comprises a main support device that basically extends over an entire length of the endoscope, wherein a distal end of the main support device comprises at least one lighting unit and two imaging devices to detect two monitoring areas, wherein each of the two imaging devices is basically arranged in such a way that it can be rotated to the outside of the main support device,
a trocar, by means of which the endoscope can enter a human body,
an additional support device, which is provided at the trocar or the main support device, wherein a distal end of the additional support device comprises an additional imaging device, wherein the additional imaging device is spaced apart in a longitudinal direction of the endoscope from the two imaging devices, and wherein the additional imaging device can be rotated to the outside of the additional support device, and wherein the additional imaging device comprises an additional lighting unit and at least an additional image sensor, wherein the additional image sensor comprises a further monitoring area, wherein the further monitoring area encompasses the two monitoring areas of the two imaging devices of the main support device,
and an image processing unit and a visualization unit, wherein the image processing unit is connected with the two imaging devices and the additional image sensor, and wherein the visualization unit is configured to show 2D image data or 3D image data of the two imaging devices or the additional image sensor, or of the two imaging devices together with the additional image sensor, wherein the additional support device is located between the trocar and the main support device, optionally resting directly at the main support device, wherein optionally the main support device and the additional support device have a cylindrical design and wherein each of the two imaging devices is arranged in such a way that it can be tilted by means of separate joints about separate rotation axis, as well as about a further pivot axis, in an orthogonal direction relative to a longitudinal extension of the main support device, wherein the rotation axis and the further pivot axis are also orthogonal to one another and wherein rotary movements about the separate rotation axes are decoupled independently of one another, and the separate rotation axes are also decoupled independently of one another.

5. The surgical robot system according to claim 4, characterized in that the additional image sensor comprises a wide-angle lens located near a distal end of the trocar when the additional image sensor is pivoted.

6. The surgical robot system according to claim 4, characterized in that the two imaging devices are arranged at the distal end of the main support device, respectively, in such a manner that they can be rotated about a rotation axis, wherein each rotation axis is aligned in a plane parallel to one another.

* * * * *